(12) United States Patent
HogenEsch et al.

US009821055B2

(10) Patent No.: US 9,821,055 B2
(45) Date of Patent: Nov. 21, 2017

(54) VACCINE ADJUVANTS

(71) Applicant: Purdue Research Foundation, West Lafayette, IN (US)

(72) Inventors: Harm HogenEsch, West Lafayette, IN (US); Yuan Yao, West Lafayette, IN (US)

(73) Assignee: PURDUE RESEARCH FOUNDATION, West Lafayette, IN (US)

( * ) Notice: Subject to any disclaimer, the term of this patent is extended or adjusted under 35 U.S.C. 154(b) by 0 days.

(21) Appl. No.: 14/935,376

(22) Filed: Nov. 7, 2015

(65) Prior Publication Data

US 2017/0128567 A1    May 11, 2017

(51) Int. Cl.
*A61K 39/39* (2006.01)
*A61K 9/14* (2006.01)
*C08B 37/00* (2006.01)
*A61K 39/145* (2006.01)
*C08B 37/18* (2006.01)
*C08G 18/08* (2006.01)
*A61K 47/69* (2017.01)

(52) U.S. Cl.
CPC ............... *A61K 39/39* (2013.01); *A61K 9/14* (2013.01); *A61K 9/145* (2013.01); *A61K 39/145* (2013.01); *A61K 47/6939* (2017.08); *C08B 37/0009* (2013.01); *C08B 37/18* (2013.01); *C08G 18/0814* (2013.01)

(58) Field of Classification Search
CPC ............ C08B 37/0009; C08G 18/0809; C08G 18/0814; A61K 9/14; A61K 49/0093
See application file for complete search history.

(56) References Cited

U.S. PATENT DOCUMENTS 5,795,582 A * 8/1998 Wright ................. A61K 39/145
                                              424/400
2015/0080220 A1 * 3/2015 Yao ........................ A61K 47/36
                                              504/358

FOREIGN PATENT DOCUMENTS

WO    WO2013/158992        10/2013
WO    WO 2013158992 A1 * 10/2013 ............. A61K 47/36

OTHER PUBLICATIONS

Santos et al (Journal of Controlled Release, May 2010, vol. 144, pp. 55-64).*
Lu et al (Journal of Controlled Release, available online Mar. 3, 2015, vol. 204, pp. 51-59).*
Nair et al (International Immunopharmacology, 2004, vol. 4, pp. 1645-1659, abstract).*
Tahara et al (Biomaterial Science, 2015, vol. 3, pp. 256-264).*
Takahashi et al (Biomaterial Science, 2013, vol. 1, pp. 842-849).*
Toita et al (Chemistry Letters, 2009, vol. 38, pp. 1114-1115).*
Toita et al (Biomacromolecules, 2010, vol. 11, pp. 397-401).*
Toita et al (Journal of Controlled Release, 2011, vol. 155, pp. 54-59).*
Effective CpG DNA delivery using amphiphilic cycloamylose nanogels: Biomaterials Science, 2015, 3, 256.
Cationic amphiphilic polysaccharide nanoballs: protein stabilization and intracellular delivery by nano-encapsulation: Biomaterials Science, 2013, 1, 842.
Cycloamylose-based Biomaterial: Nanogel of Cholesterol-bearing cationic Cycloamylose for siRNA Delivery: Chemistry Letters vol. 38, No. 11 (2009).
Polysaccharide nanogel gene delivery system with endosome-escaping function: Co-delivery of plasmid DNA and pohospholipase A2: Journal of Controlled Release 155 (2011) 54-59.

* cited by examiner

*Primary Examiner* — Mark V Stevens
(74) *Attorney, Agent, or Firm* — Purdue Research Foundation; Yonghao Hou

(57) ABSTRACT

The present invention provides a new adjuvant for administering vaccines.

17 Claims, 14 Drawing Sheets

VACCINE ADJUVANTS

TECHNICAL FIELD

The present disclosure generally relates to compositions of adjuvants and methods of using the same.

BACKGROUND

This section introduces aspects that may help facilitate a better understanding of the disclosure. Accordingly, these statements are to be read in this light and are not to be understood as admissions about what is or is not prior art.

Vaccines are increasingly formulated with antigens consisting of subunits of microbial pathogens generated through chemical processing or genetic engineering to ensure the safety of vaccines. Unfortunately, these vaccine antigens are poorly immunogenic and adjuvants are added to stimulate an effective immune response. Adjuvants work, at least in part, by increasing the antigen uptake and by promoting the activation of dendritic cells (DCs), a critical step in the initiation of the immune response. The most widely used adjuvants in human and veterinary vaccines are aluminum-containing adjuvants which generally induce a good antibody response, have an excellent long term safety profile, and are relatively inexpensive. However, aluminum adjuvants are ineffective in inducing a cell-mediated immune response; are inactivated by freezing; can have a detrimental effect on the stability of vaccine antigens; and are associated with local adverse vaccine reactions. In addition, aluminum is not biodegradable, and most of it is excreted via the kidneys and sweat glands. New adjuvants need to stimulate the appropriate immune response, but the single most important consideration is safety. In addition, adjuvants need to be biodegradable, compatible with various antigens, and inexpensive.

SUMMARY OF THE INVENTION

The present invention provides a composition comprising an adjuvant comprising a core molecule comprising binding moieties and ranging in size between 10 nanometers and 300 nanometers, a hydrophobic group bound to the core molecule through the binding moieties, and a positively charged group bound to the core molecule by the binding moieties comprising an overall positively charged molecule; wherein the core is selected from the group of dendrimer, dendrimer-like material, chitosan, or highly branched alpha-D-glucan such as amylopectin, phytoglycogen, or glycogen.

Figure 1A:
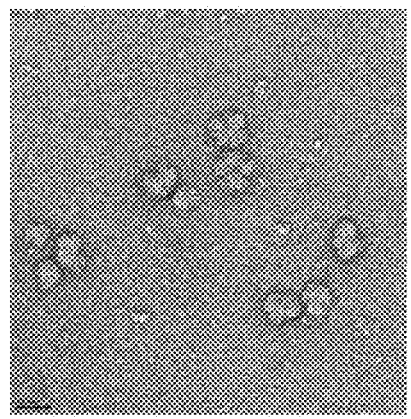
FIG. 1A-1D, shows physical characterization of the adjuvant nanoparticles with (1A) showing a TEM of a 0.01% (w/v) solution of the adjuvant nanoparticles and the size bar is 50 nm, where (1B) shows the diameter of the adjuvant nanoparticles as determined by dynamic light scattering, where (1C) shows the zeta potential of the adjuvant nanoparticles, and (1D) shows adsorption of negatively charged ovalbumin (OVA) and lack of adsorption of positively charged lysozyme to the adjuvant nanoparticles. Mean±SEM of three independent experiments.
Figure 1B:
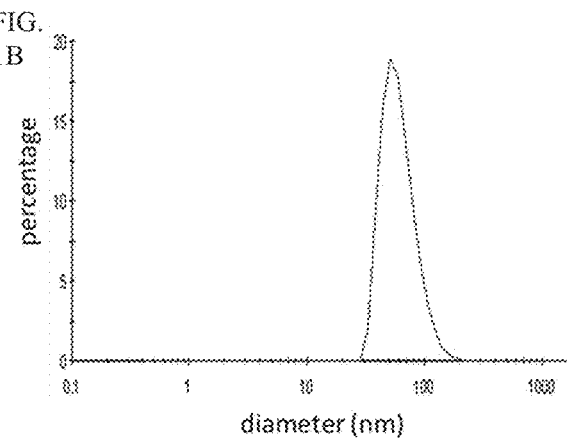
Figure 1C:
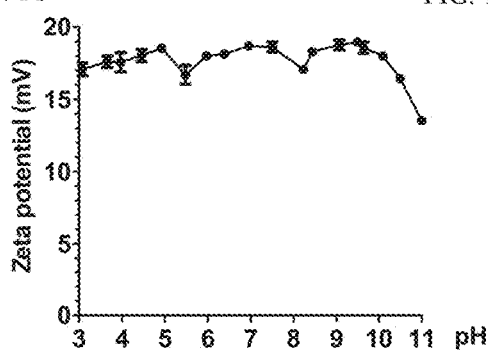
Figure 1D:
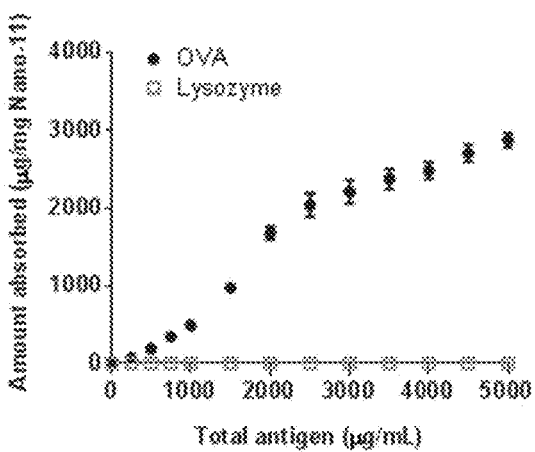

Reference to figure numbers may be preceded by "FIG.", "FIG", or "Figure", interchangeably.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

The disclosure provides details on a new formulation of a composition for an adjuvant. The adjuvant composition comprises two units. In certain aspects, the adjuvant comprises three units. The adjuvant is designed to be adsorptive and biodegradable. The adjuvant may be covalently bound to an antigen, or the adjuvant may be connected to the antigen by a positive-negative attraction. The adjuvant displays a plurality of hydrophobic moieties, and a plurality of positively charged moieties. These two distinct moieties may be replaced by a single moiety which possesses both of these properties.

A novel composition of an adjuvant is described along with methods of use and formulations. The adjuvant is a plurality of nanoparticles comprising units. In certain embodiments the adjuvant comprises two units. In certain embodiments the adjuvant comprises three units. The overall size of the adjuvant may range between 15 and 300 nanometers (nm). The molecule includes a core unit, or the first unit. The core unit may be made of various materials as later described, but requires binding sites for at least the second unit and third unit if applicable to be linked to the core molecule. The second unit is present to make the overall composition hydrophobic and/or positively charged. This may be accomplished with two or more distinct additional units. A second unit, separate from the first, core unit, which provides a hydrophobic group, and a third unit which is used to provide an overall positive charge for the composition. The overall positive charge serves two purposes. The first purpose is to adsorb negatively charged proteins in vitro or in vivo, and the second purpose is to resist aggregation of the nanoparticles. There are other benefits to having a nano-sized hydrophobic, and overall positively charged nanoparticle as an adjuvant as will be described in the additional applications of use for the adjuvant.

The first unit of the adjuvant is the core molecule. In certain embodiments the core molecule is a sphere or sphere-like shape ranging in size between about 10 nm and about 250 nm, 20 nm to 230 nm or 30 nm to 110 nm. The desired material for the core molecule comprises a material that is biodegradable. The core may comprise material made up of dendrimer or dendrimer-like materials, polysaccharides such as chitosan, starch, glycogen, and phytoglycogen (PG), and polyethylene glycol (PEG), as well as their derivatives, or a combination thereof. In certain embodiments the core material comprises branched alpha-D-glucan such as amylopectin. The core material comprises binding sites for attaching a second unit, and if needed a third unit or additional units. An example of a binding site is hydroxyl group (—OH), where the hydrogen is removed in the linking process so that the second, and if needed third or additional unit are covalently attached to the core (i.e. the first unit).

Phytoglycogen is one type of highly branched alpha-D-glucan. The term "highly branched alpha-D-glucan" (highly branched a-D-glucan), as used herein, refers to a highly branched polysaccharide formed with alpha-D-glucosyl units, such as glycogen, phytoglycogen, amylopectin, dextran, or modified forms thereof. In some embodiments, the polysaccharides are formed by alpha-D-1,4 and alpha-D-1,6 glucosidic linkages. However, in other embodiments, chemical modification (e.g., pyrodextrinization) can be used to provide highly branched alpha-D-glucans including other types of linkages, such as alpha-D-1,2 and alpha-D-1,3 linkages. The highly branched alpha-D-glucan can be obtained, derived, or extracted from a plant material, a microbe (e.g., bacterium), or a human or non-human animal, or synthesized from glucose, glucans, or other materials. In one example, the highly branched alpha-D-glucan comprises glycogen, phytoglycogen, amylopectin, and/or modified forms thereof, such as with modifications with octenyl succinate (OS) or polyethylene glycol (PEG).

As used herein, a highly branched polysaccharide is a polysaccharide having a branch density of at least about 4%. For the branched alpha-D-glucans, the branch density is defined as the percentage of the amount of branching points, which can be formed through 1, 2-, 1,3-, and/or 1,6-glucosidic linkages, over the total amount of glucosidic linkages. In some embodiments, the branch density of the highly branched alpha-D-glucans can range from about 5% to about 30%. In other embodiments, the branch density is at least 5%, at least 6%, at least 7%, or at least 8%. In other embodiments, the branch density can range for example, between about 7% to about 16%. For example, the branch density of amylopectin can be about 4%-6%, and the branch density of glycogen and phytoglycogen can be about 8%-11%. For example, for glucans that contain only alpha-D-1,4 and alpha-D-1,6 glucosidic linkages, branch density can be determined by comparing the number of alpha-D-1,4 and alpha-D-1,6 glucosidic linkages as follows: percentage branch density=the number of alpha-D-1,6 glucosidic linkages/(the number of alpha-D-1,4 glucosidic linkages+the number of alpha-D-1,6 glucosidic linkages)*100. In general, branch density is the percentage of branching points based on all glucosidic linkages in the glucan molecule.

In some embodiments, the highly branched alpha-D-glucan has a dendritic structure (also called dendrimer-like structure). In a dendritic structure, the polysaccharide chains are organized globularly like branches of a tree originating from a central location that acts as a primer at the core of the structure. In some embodiments the highly branched alpha-D-glucan can be modified to include functional groups selected from acetate, phosphate, octenyl succinate, succinate, hydroxypropyl, hydroxyethyl, cationic groups such as those containing quaternary ammonium cations (e.g. formed using 2,3-epoxypropyl trimethylammonium chloride, EPTAC, and (3-chloro-2-hydroxypropyl) trimethylammonium chloride, CHPTAC), carboxymethyl, polyethylene glycol (PEG), polyethylene oxide, polypropylene glycol, polypropylene oxide, or a combination of above. In some embodiments, the highly branched alpha-D-glucan can also be modified by bleaching, acid hydrolysis, oxidation, pyrodextrinization, or a combination of above. Additional information about the highly branched alpha-D-glucan phytoglycogen can be found in WO 2013/158992 the contents of which are incorporated herein by reference.

The second unit is a plurality of hydrophobic binding moieties. The second unit is made up of hydrophobic elements. This can be achieved by grafting a substitution group that contains one or multiple hydrophobic groups such as, but not limited to, alkyl group, alkene group, benzene group, sterol group, hydrophobic amino acids, cyclodextrins, hydrocarbon groups (e.g. aromatic hydrocarbons (arenes), alkanes, alkenes, cycloalkanes and alkyne-based compounds), or hydrophobic chains. In one aspect the plurality of hydrophobic binding moieties includes carbon double bond carbon (C=C) chains ranging between four and fourteen carbons long. In one aspect the second unit is a plurality of octenyl succinate (OS) groups.

The third unit is a plurality of positively charged binding moieties. The third unit is made up of positively charged elements. This can be achieved by using a positively charged amino acid, a peptide chain including positively charged amino acids, or positively charged synthetic peptides. This can also be achieved by using a unit that includes an amine group, ammonium ion, and quaternary ammonium cationic group. The cationic (i.e. positively charged) group may be an inorganic group such as arsaniumyl group, azaniumyl group, diazyn-1-ium-1-yl group, phosphaniumyl group, stibaniumyl group, sulfaniumyl group, or tellaniumyl group. The cationic group may also be an organic group such as α-amino-acid residue cation, 3'-(L-arginyl)adenylyl(1+), 3'-(L-lysyl)adenylyl(1+) group, 5-aminomethyl-2-thiouridine residue(1+), 7-methylguanosin-5'-yl group, 7-methylguanosine 5'-triphosphate group, N,N-dimethyl-L-alaniniumyl group, N2,N2,N7-trimethylguanosine 5'-triphosphate group, L-alaniniumyl group, L-argininiumyl(2+) group, L-asparaginiumyl group, L-cysteiniumyl group, L-glutaminiumyl group, L-histidiniumyl group, L-isoleuciniumyl group, L-leucyl(1+) group, L-lysiniumyl(2+) group, L-phenylalaniniumyl group, L-proliniumyl group, L-pyrrolysiniumyl group, L-seriniumyl group, L-threoniniumyl group, L-tryptophaniumyl group, L-tyrosiniumyl group, L-valiniumyl group, [4]-D-GlcpN-(1→](1+) residue, amino-acid cation residue, glyciniumyl group, and phosphocholine group. The cationic group may also be related to, or contain the cationic moiety of benzalkonium chloride, benzehonium chloride, methylbenzethonium chloride, cetalkonium chloride, cetylpyridinium chloride, cetrimonium, cetrimide, choline, dofanium chloride, tetraethylammonium bromide, dideclydimethylammonium chloride, domiphen, For example, the cationic group can be one of those generated by reacting a hydroxyl group with (3-chloro-2-hydroxypropyl) trimethylammonium chloride (CHPTAC).

The second and third units, if present, are covalently linked, directly or through another group, to the first unit or core molecule. The second and third unit are distributed over the entire core molecule and may be found in a ratio of about 1/5 second unit:about 4/5 third unit, about 2/5 second unit:about 3/5 third unit, about 1/4 second unit:about 3/4 third unit, about 1/3 second unit:about 2/3 third unit, or about 1/6 second unit:about 5/6 third unit.

When combining the first and second or first, second, and third units together, the reaction generates an overall composition. In certain embodiments the overall composition may range in size of 15 nm to 275 nm in diameter. In some aspects the overall composition ranges in size of 20 nm to 200 nm. In some aspects the overall composition ranges in size of 40 to 100 nm. In some aspects the composition ranges in size of 40 to 80 nm.

The composition may be administered to any mammal or other vertebrate species. As non-limiting examples of a mammal includes human, dog, cat, horse, swine, sheep and cows. Non-limiting examples of other vertebrates include chicken and fish.

The composition may be administered up to 200 ug per Dose (ug/Dose). In certain embodiments the composition may be administered at about 25 ug/Dose, about 50 ug/Dose, about 75 ug/Dose, about 100 ug/Dose, about 125 ug/Dose, about 150 ug/Dose, about 175 ug/Dose, or about 200 ug/Dose. In other embodiments the composition may be administered from about 10 ug/Dose to 10 mg/Dose depending on the mammal size and weight. The dose range may be about 10 ug/Dose to about 25 ug/Dose. In other aspects the dose may range from about 200 ug/Dose to about 1 mg/Dose, about 1 mg/Dose to about 2 mg/Dose, about 2 mg/Dose to about 3 mg/Dose, about 3 mg/Dose to about 4 mg/Dose, about 4 mg/Dose to about 5 mg/Dose, about 5 mg/Dose to about 6 mg/Dose, about 6 mg/Dose to about 7 mg/Dose, about 7 mg/Dose to about 8 mg/Dose, about 8 mg/Dose to about 9 mg/Dose, or about 9 mg/Dose to about 10 mg/Dose. It is understood that the amount per dose and the number of doses will be determined by one of skill in the art.

The composition may be administered into the muscle, subcutaneously or intradermally. Other applications include mucosal vaccination and DNA vaccination which are useful against viruses. One of skill in the art will recognize that there are other uses for the described composition. Other applications include immunotherapy of cancer, immunotherapy of allergy, and gene delivery. The adjuvant nanoparticles can be combined with other immunomodulators to enhance the ability to elicit specific immune responses. The positive charge of the adjuvant nanoparticles enables the electrostatic adsorption of negatively charged immunostimulatory molecules including, but not limited to, poly(I:C), monophosphoryl lipid A, and CpG DNA oligonucleotides. The adsorption of these molecules to the nanoparticles can enhance the potency and reduce systemic toxicity. Such combinations may be used in the development of therapeutic vaccines against cancer and immunotherapy of allergic diseases. The size of the adjuvant nanoparticles may range between 15-300 nm, and is appropriate for co-delivery of adsorbed antigen and immunostimulatory molecules to cells.

The positive charge of the adjuvant nanoparticles can also be employed to adsorb DNA molecules due to DNAs negative charge, and may be used to improve the delivery of genes into cells. This will enhance the efficacy of DNA vaccines as well as gene therapy. Fragments of DNA or RNA, whether single or double stranded may be delivered to the cell to cause an effect. At least one peptide or multiple peptides may be coupled to the adjuvant nanoparticle for delivery into a cell to elicit a response from the cell. The sequence of DNA or RNA, and the peptides that would of interest for delivery are dependent upon the application. As an example, DNA from a virus or transcribed RNA from a virus could be delivered to cause a response to recognize it as foreign, or DNA could be delivered as a form of gene therapy into a cell, whether transient or stable. The DNA may have a recognizable repeat or sequence to direct it to the targeting sequence for insertion, or for recognition by an enzyme. The DNA or RNA may be packaged in such a way to prevent it from degradation when coupled to the adjuvant.

The peptides could be an antibody, a growth factor, a synthetic non-naturally occurring peptide, a ligand, a kinase, or a transcription factor. The peptides may be packaged in such a way to prevent degradation while coupled to the adjuvant. The amount of DNA, RNA, peptide, or biomolecule to deliver to an animal is determined by one of ordinary skill in the art.

The adjuvant could also be used to deliver a small molecule or drug to the immune cells to increase or decrease the immune systems response. The combination of a small molecule and the adjuvant may be useful to ramp up a weak immune system, or to reduce the immune systems overall response in say an animal with extensive inflammation. The amount of drug delivered with the adjuvant nanoparticle is determined by someone of ordinary skill in the art to provide an effective amount.

The adjuvant may be used in to replace the current adjuvant in all currently available and future vaccines including but not limited to; vaccines for Ebola, Avian flu, influenza, Poliomyelitis, Measles, Mumps, Rubella, tetanus, Canine distemper, Canine adenovirus 2, Canine parvovirus, Canine parainfluenza, *Leptospira* bacterin-CI, Feline panleukopenia, Feline rhinotracheitis, Feline caliciviruses, BVD, 8-way *Clostridium* bacterin, *Clostridium* bacterin, S-way *Leptospira* bacterin, Parainfluenza 3, EEE, WEE, Equine rhinopneumonitis, West Nile virus, *Erysipelas* bacterin, Rabies, IHNV, VHSV, Diphtheria, Tetanus, whole cell pertussis (DTwP), acellular Pertussis (DTaP), Tdap, Hepatitis A, Hepatitis B, Hib, Measles, Mumps, Rubella (MMR), Meningococcal, Pneumococcal, Polio, Varicella, HPV, all subsets of HPV, Hepatitis C, Hepatitis E, Anthrax, Brucellosis, Chikungunya, Ciguatera Fish Poisoning, Denuge, Echinococcosis, Hantavirus, Hand foot and mouth disease, chicken pox, Chagas disease, cholera, Crimean-Congo Hemorrhagic Fever, Epidemic Typhus, Histoplasmosis, hookworm/cutaneous larva migrans, intestinal parasites, Japanese encephalitis, lassa fever, legionnaires disease, leishmaniasis, leptospirosis, lyme disease, lymphatic filariasis, malaria, Marburg virus disease, melioidosis, meningococcal meningitis, middle east respiratory syndrome, murine typhus, plague, Rift valley fever, river blindness/onchocerciasis, Ross river fever, schistosomiasis, scrub typhus, sexually transmitted infections, sleeping sickness/African trypanosomiasis, tick-borne encephalitis, tick-borne spotted fevers, traveler's diarrhea, tuberculosis, typhoid fever, valley fever/coccidioidomycosis, viral encephalitis, yellow fever, Zika fever, whooping cough, adenovirus types 4 and 7, small pox, diphtheria, HIV, other viruses, other bacteria, and other parasites.

The adjuvant may be used to help induce an immune response and make a vaccine more effective for all known diseases treatable and untreatable, with some previously listed, and future diseases not yet identified.

Formulation: An antigen and adjuvant are delivered together in the application. In certain applications the adjuvant and antigen may be covalently linked prior to delivery. The adjuvant coupled to at least one antigen is delivered by an acceptable delivery vehicle known in the art. The adjuvant may be a heterogeneous of varying adjuvant nanoparticle size ranges or may be a homogeneous mixture of one size of nanoparticle. The amount, size range, and delivery vehicle will be dependent on the disease type, antigen, and animal receiving the vaccine. One of ordinary skill in the art will recognize these parameters and prepare the vaccine accordingly.

One exemplary process to synthesize the adjuvant nanoparticles includes Sweet corn kernels from a su1 mutant strain known as Silver Queen, were ground and mixed with six weights of deionized water. The suspension was homogenized and centrifuged at 8000 g for 20 min. The supernatant was passed through a 270-mesh sieve. Three volumes of ethanol were added to the supernatant to precipitate polysaccharides. After centrifugation and decanting, the precipitate was suspended using ethanol and filtrated to dehydrate for three cycles. The solid material obtained after removing the residual ethanol was phytoglycogen (PG). To the dispersion (20%) of PG (20 g of PG in 100 mL water), 1.8 g of octenyl succinic anhydride (OSA) were gradually added in 2 h. The pH was maintained between 8.5 and 9.0 using 5% NaOH. The reaction was carried out at 50° C. and terminated after 24 h by reducing the pH to 6.0-7.0 using 10% HCl. To the dispersion, 3 volumes of ethanol were added, and the precipitate was collected and subjected to three cycles of dispersion-filtration using ethanol. The solids obtained were placed in a fume hood to remove residual ethanol. The dry material collected is phytoglycogen octenyl succinate (PG-OS). The PG-OS material was ground to pass 80-mesh sieve, and 10 g of PG-OS was dispersed in 50 mL deionized water to form 20% dispersion. To this dispersion, 10 mL of (3-Chloro-2-hydroxypropyl)-trimethylammonium chloride (CHPTAC) was added over a period of 2 h while maintaining pH 11 using 5 M NaOH. The reaction was carried out at 50° C. for 24 h with continuous stirring. Thereafter, the pH was adjusted to 6.0-7.0 using 10% HCl to terminate the reaction. The mixture was precipitated by adding 3 volumes of ethanol and followed by a three-time dispersion-filtration washing procedure using ethanol. The collected solid was placed in a fume hood to remove residual ethanol. The dry material collected is PG-OS-CHPTAC (the adjuvant nanoparticles). The term "CHPTAC" not only indicates the chemical 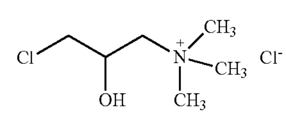 compound of (3-Chloro-2-hydroxypropyl)-trimethylammonium chloride (structure shown above), but also indicates the cationic group generated by reacting this compound with the hydroxyl group of, for example, phytoglycogen, glycogen, amylopectin, chitosan, and dextran. In this document, the word "cationic" has the same meaning as "positively charged".

EXAMPLES

Referring now to FIG. 1A-1D, the adjuvant in suspension is examined by electron microscopy showing spherical particles with an irregular surface, giving them a cauliflower-like appearance as shown in FIG. 1A. The particles were single or in pairs, and rarely formed larger aggregates. The particles were fairly uniform in size ranging from 30-110 nm as shown in FIG. 1B. The nanoparticles were positively charged and the zeta potential was stable at +16-19 mV over a pH range of 3-10 as shown in FIG. 1C. The positive charge is likely the reason for the dispersion of the adjuvant nanoparticles in solution. The adjuvant nanoparticles adsorbed ovalbumin which is negatively charged at neutral pH, but not lysozyme which is positively charged suggesting that the adsorption is largely regulated by electrostatic mechanisms as shown in FIG. 1D. The irregular surface potentially increases the adsorptive surface of the adjuvant nanoparticle and may contribute to the high adsorptive capacity of the adjuvant nanoparticle.

Figure 2:
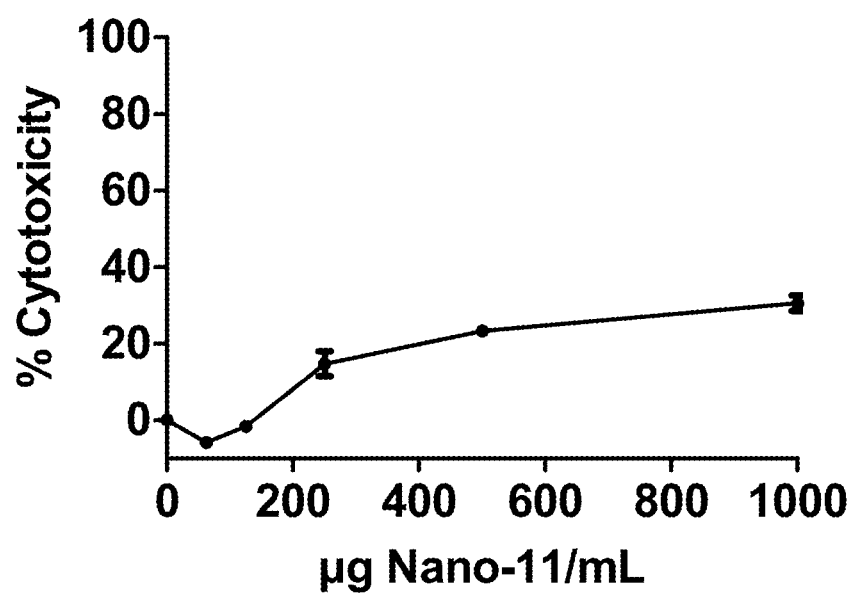
FIG. 2 shows cytotoxicity of the adjuvant nanoparticles, using dendritic cells incubated for 48 hours with indicated concentrations of the adjuvant nanoparticles, and the cytotoxicity was determined by release of lactate dehydrogenase (LDH) in the supernatant.

Referring now to FIG. 2, Bone marrow derived dendritic cells (BMDCs) generated from BALB/c mice were incubated with increasing concentrations of the adjuvant nanoparticle and cell damage was assessed by the concentration of LDH in the supernatant. A modest increase of LDH was observed at the adjuvant nanoparticle concentrations of 250 µg/mL and higher indicating that the adjuvant nanoparticle has a low level of cytotoxicity.

Figure 3:
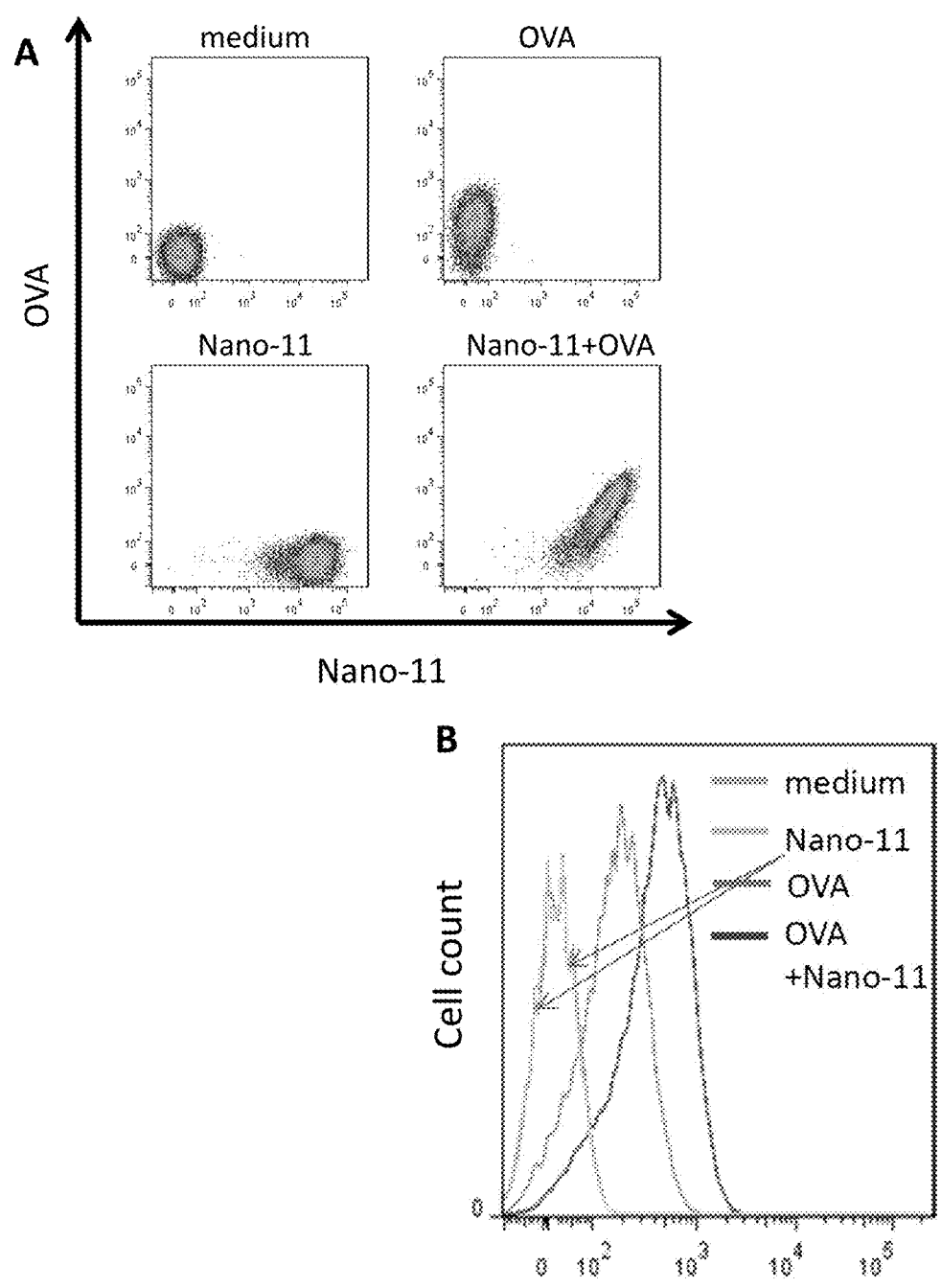
FIG. 3 shows the adjuvant nanoparticles enhance the uptake of adsorbed antigens where DCs were incubated for 2 hours with soluble FITC-labeled ovalbumin (OVA), AF647-labeled adjuvant nanoparticles, or ovalbumin adsorbed to AF647-labeled adjuvant nanoparticles, and examined by flow cytometry, with Panel A showing a dot plot and Panel B showing a histogram for FITC-OVA. Data are representative of two independent experiments.
Figure 9:
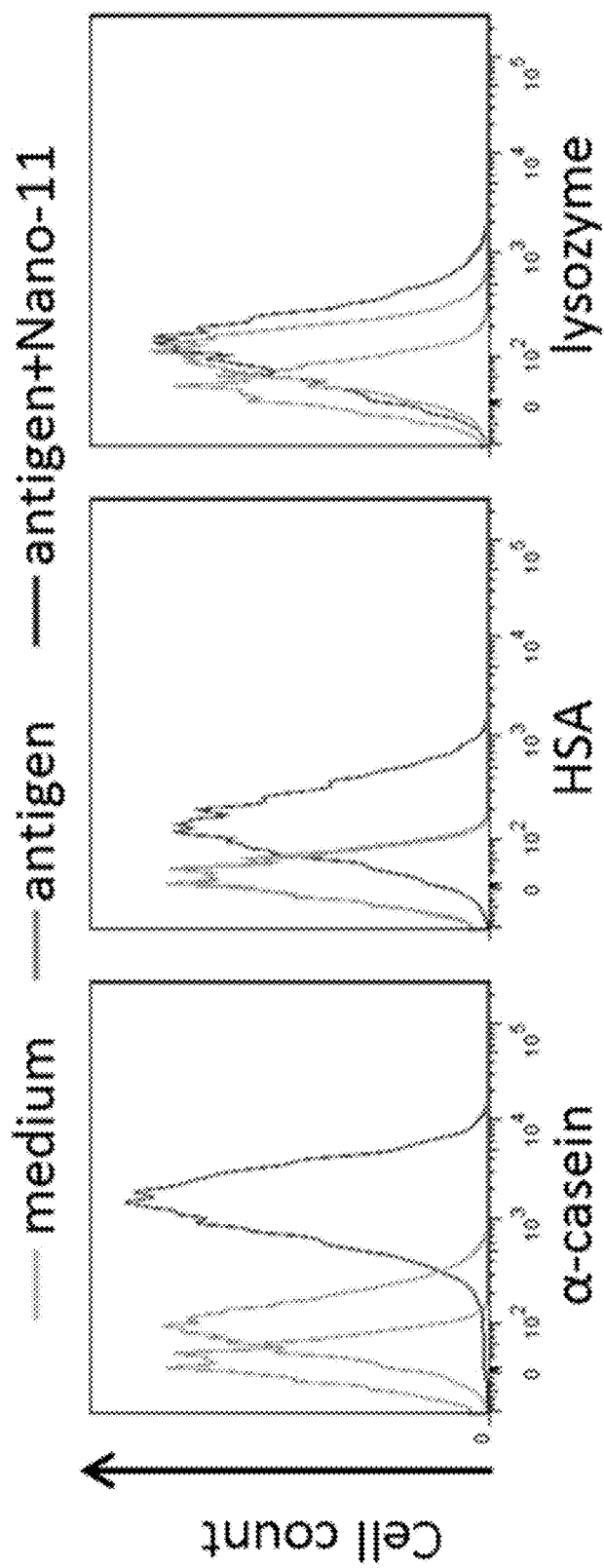
FIG. 9 shows three graphs that demonstrate that when mixing with the adjuvant nanoparticles increased the uptake of negatively charged proteins, alpha-casein and human serum albumin, wherein contrast, the positively charged the adjuvant nanoparticles did not enhance the uptake of positively charged lysozyme.

Referring now to FIG. 3, to examine the effect of the adjuvant nanoparticle on antigen uptake, BMDCs were incubated with FITC-labeled OVA and AF647-labeled adjuvant nanoparticle. After two hours of incubation with soluble OVA, a small amount of OVA was detected in BMDCs. This is consistent with previous studies that have shown that soluble OVA is taken up by BMDCs via the mannose receptor. When BMDCs were incubated with the adjuvant nanoparticle adsorbed OVA, the amount of OVA inside DCs was greatly increased and nearly every cell contained OVA. OVA and the adjuvant nanoparticle colocalized in the cells, suggesting that OVA remained associated with the adjuvant nanoparticle after uptake by dendritic cells (DCs). The OVA-adjuvant nanoparticle complexes were concentrated in the perinuclear area of the cells. To quantify the percentage of DCs that had taken up OVA/adjuvant nanoparticle and their amount inside cells, flow cytometry was used. BMDCs incubated with soluble OVA had a modest increase of fluorescence consistent with the confocal microscopy results. Following incubation with labeled adjuvant nanoparticles and OVA, both the green and red fluorescence increased indicating that the majority of cells had taken up the adjuvant nanoparticle/OVA complexes and that the adjuvant nanoparticles enhanced the intracellular delivery of the adjuvant nanoparticles as shown in FIG. 3. The effect of the adjuvant nanoparticles on antigen uptake was tested with other proteins. Mixing with the adjuvant nanoparticles increased the uptake of two other negatively charged proteins, alpha-casein and human serum albumin as shown in FIG. 9. In contrast, the positively charged the adjuvant nanoparticles did not enhance the uptake of positively charged lysozyme (FIG. 9). In aggregate, these experiments demonstrate that the adjuvant nanoparticles enhance the delivery of electrostatically adsorbed proteins to BMDCs.

Figure 4:
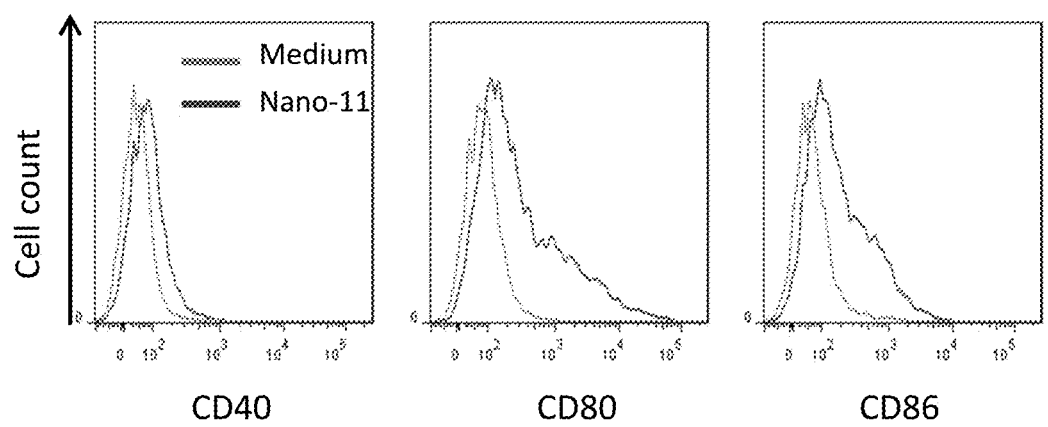
FIG. 4 shows the adjuvant nanoparticles enhance the expression of CD80 and CD86 on DCs where DCs were incubated with either 250 µg/mL of the adjuvant nanoparticles or medium control for two days and the expression of CD40, CD80, and CD86 was measured by flow cytometry. Data are representative of three independent experiments.
Figure 5:
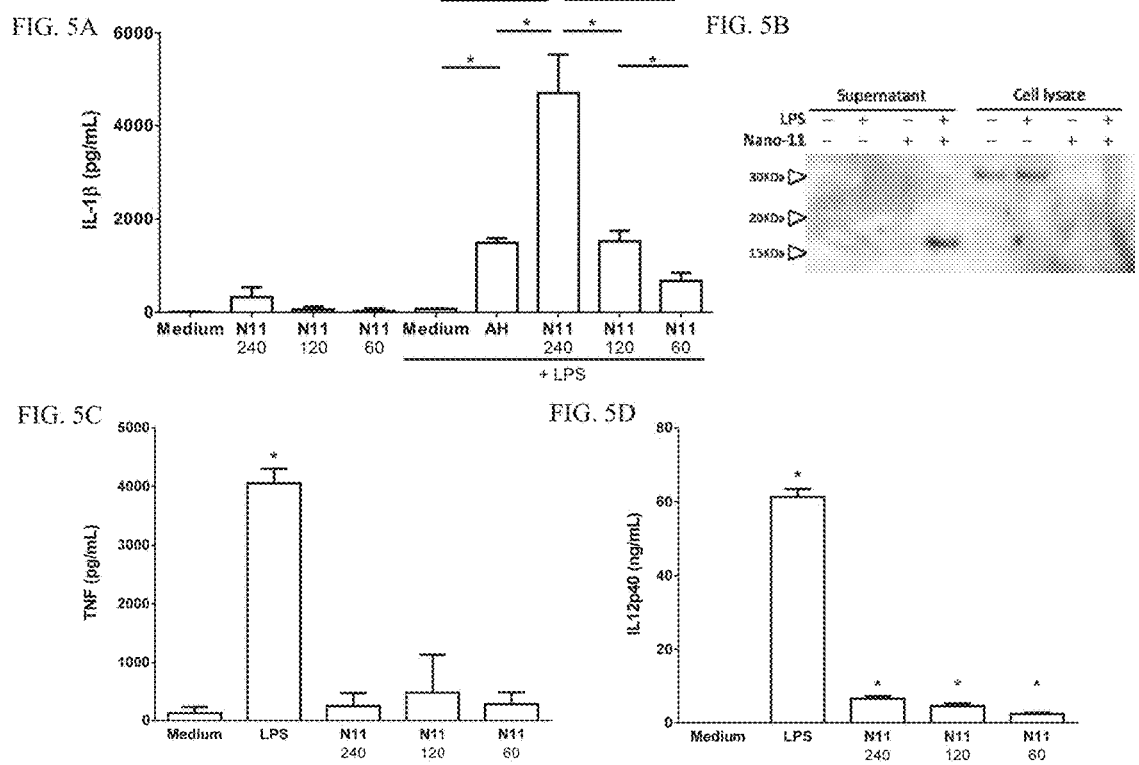
FIG. 5A-5D shows the adjuvant nanoparticles induce secretion of IL-1β and IL-12p40 where DCs were incubated with medium only, LPS (100 ng/mL) or the adjuvant nanoparticles at 60, 120 and 240 µg/mL for 2 days and supernatants were analyzed for cytokines, with (5A) showing IL-1β was induced in DC primed with LPS and exposed to aluminum hydroxide adjuvant (AH) and the adjuvant nanoparticles. *p<0.05; (5B) shows the secreted IL-1β is 17 kDa as indicated by the immunoblot; (5C) shows the adjuvant nanoparticles does not induce significant secretion of Tumor Necrosis Factor (TNF), *p<0.05 LPS vs. medium; and (5D) shows the adjuvant nanoparticles induce increased secretion of IL-12p40*p<0.05 vs. medium.
Figure 6:
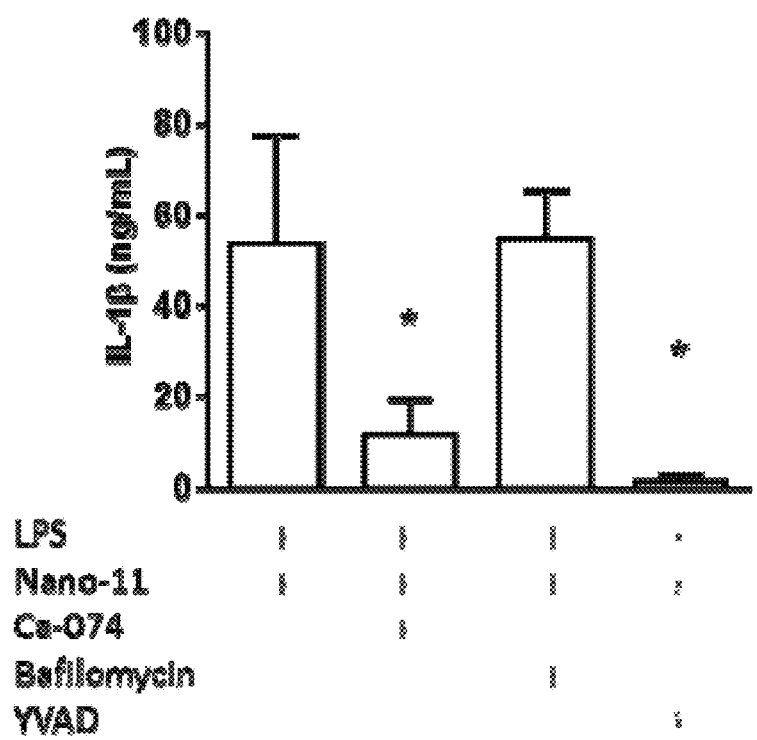
FIG. 6 shows the secretion of IL-1β by the adjuvant nanoparticles is dependent on cathepsin B and caspase-1 where DCs were incubated with the indicated chemicals followed by LPS and the adjuvant nanoparticles. Supernatants harvested after 48 h were analyzed for IL-1β. Bars represent the average±SEM of four independent experiments.

Referring now to FIGS. 4, 5 and 6, in addition to increasing delivery of antigen to DCs, a successful adjuvant also needs to promote their activation during which DCs digest the endocytosed antigen into peptides, load them onto MHC molecules (signal 1), and present them together with costimulatory molecules (signal 2) and cytokines (signal 3) to T cells, thus triggering an immune response.

Figure 10:
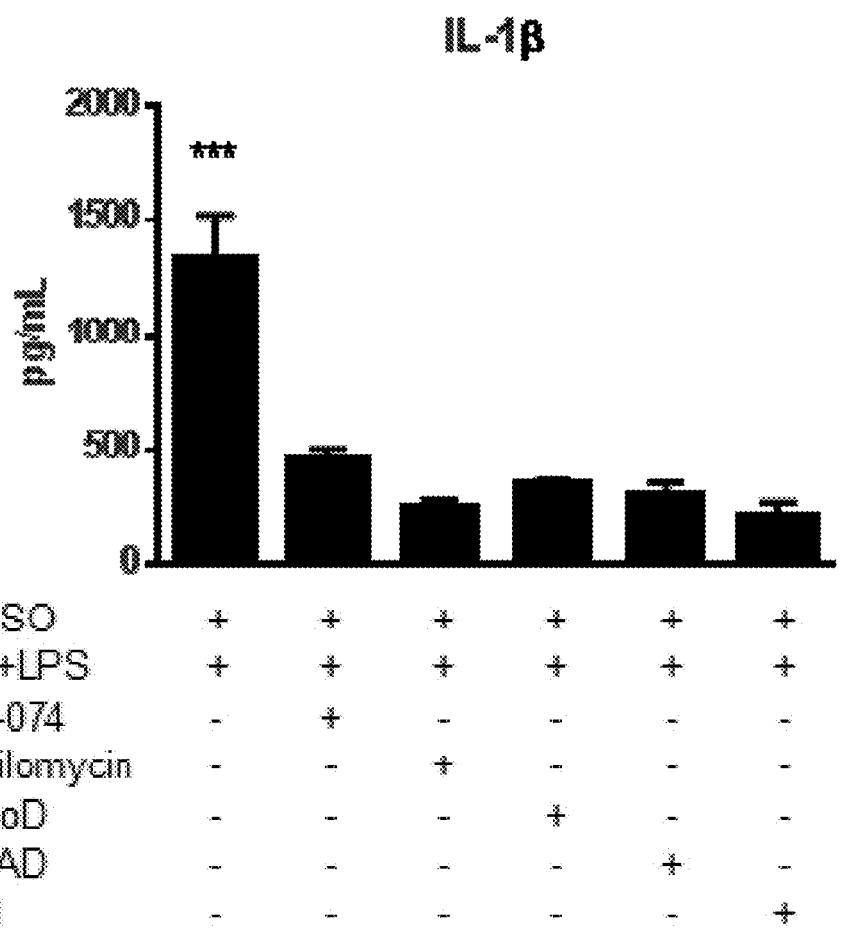
FIG. 10 is a bar graph that shows that the secretion of IL-1β by aluminum adjuvant is dependent on cathepsin B, acidification of the phagosome, and caspase-1 where DCs were incubated with the indicated chemicals followed by LPS and the adjuvant. Supernatants harvested after 48 h were analyzed for IL-1β.
Figure 11:
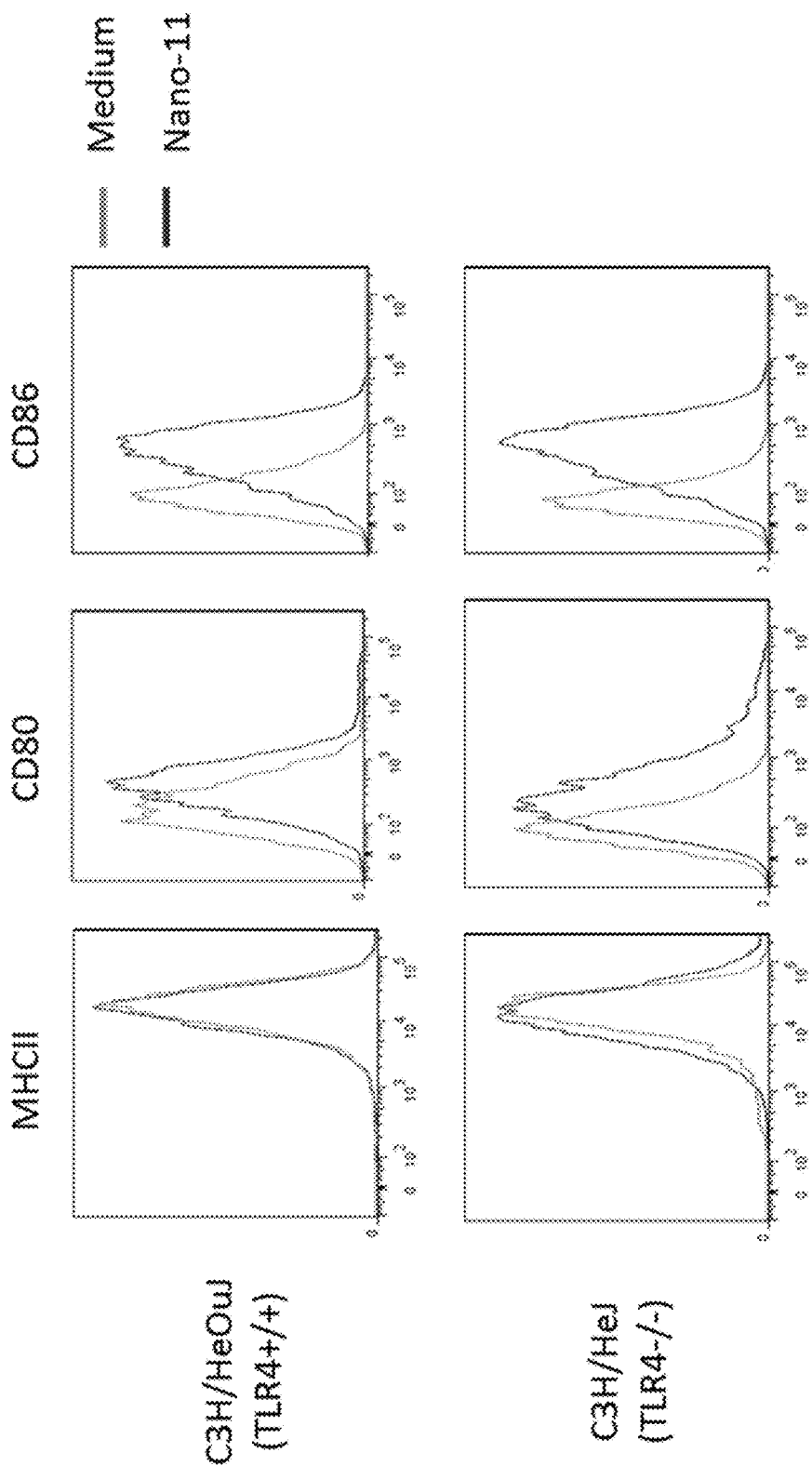
FIG. 11 shows six graphs demonstrating the increased immune response in DCs was not caused by LPS contamination of the adjuvant nanoparticles because a similar increase in expression of CD80 and CD86 was observed in DCs derived from bone marrow of C3H/HeJ mice, a strain deficient in TLR4 making it unable to respond to LPS, compared with its wild type counter mate C3H/HeOuJ mice.

Incubation of BMDCs with the adjuvant nanoparticles for two days slightly increased expression of CD40 and induced a marked increase of the expression of CD80 and CD86 as shown in FIG. 4. This was not caused by LPS contamination of the adjuvant nanoparticles because a similar increase in expression was also observed in DCs derived from bone marrows of C3H/HeJ mice, a strain deficient in TLR4 making it unable to respond to LPS, comparing with its wild type counter mate C3H/HeOuJ mice as shown in FIG. 10.

BMDCs were incubated with different concentrations of the adjuvant nanoparticles, with or without previous LPS priming to examine the effect on cytokine secretion. The adjuvant nanoparticles induced the secretion of IL-1β, a major proinflammatory cytokine, in a concentration dependent fashion as shown in FIG. 5A. At the highest dose (240 µ/mL) used in these experiments, the secretion of IL-1β exceeded that induced by aluminum hydroxide adjuvant, a potent inducer of IL-1β. Because the ELISA does not distinguish between the inactive 31 kD form of IL-1β and the active 17 kD form, a Western blot was used to verify that the measured protein was the 17 kD IL-1β as shown in FIG. 5B. The adjuvant nanoparticles had no effect on the secretion of TNF by BMDCs as shown in FIG. 5C. However, exposure of BMDCs to the adjuvant nanoparticles induced the secretion of IL-12p40, a component of IL-12p70 and IL-23, in a dose-dependent manner although not to the same level as LPS as shown in FIG. 5D.

Figure 7:
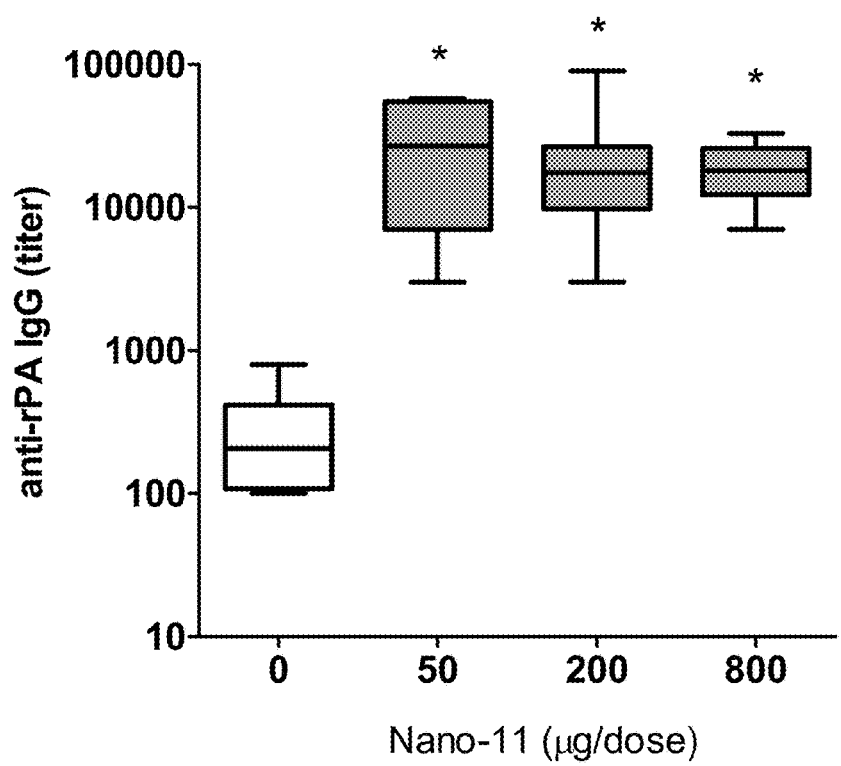
FIG. 7 shows the adjuvant nanoparticles enhances the antibody response to adsorbed antigen where mice were injected twice with the adjuvant nanoparticles at the indicated dose and 2 µg/dose recombinant protective antigen (rPA). The antibody titer was determined by ELISA. Box indicates 5-95% confidence interval and median. *p<0.01 vs. soluble rPA.
Figure 13:
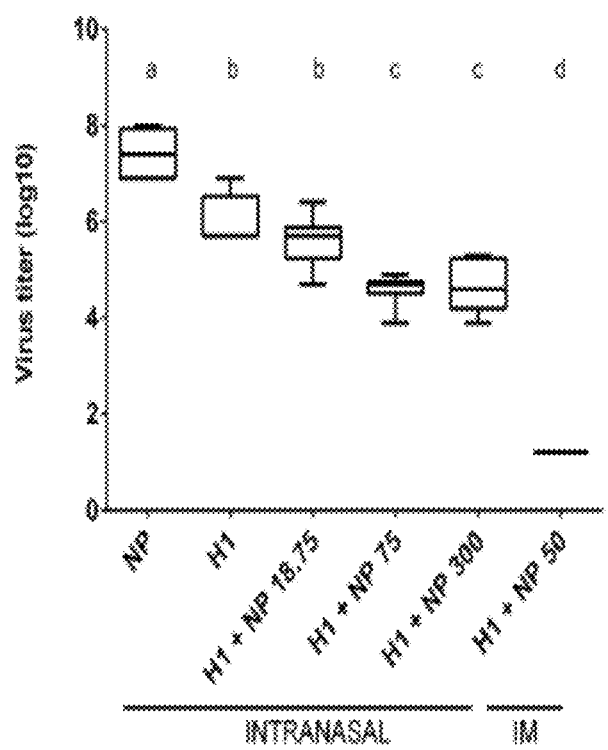
FIG. 13 is a graph showing protection against viral infection in mice immunized with Nano-11; mice were immunized with 3.375 ug of hemagglutinin (H1) via intranasal inoculation (4 doses) or 2.25 ug H1 via intramuscular injection (3 doses). The dose of Nano-11 (NP) is given in ug. Mice were challenged with homologous virus 2 weeks after the last inoculation.
Figure 14:
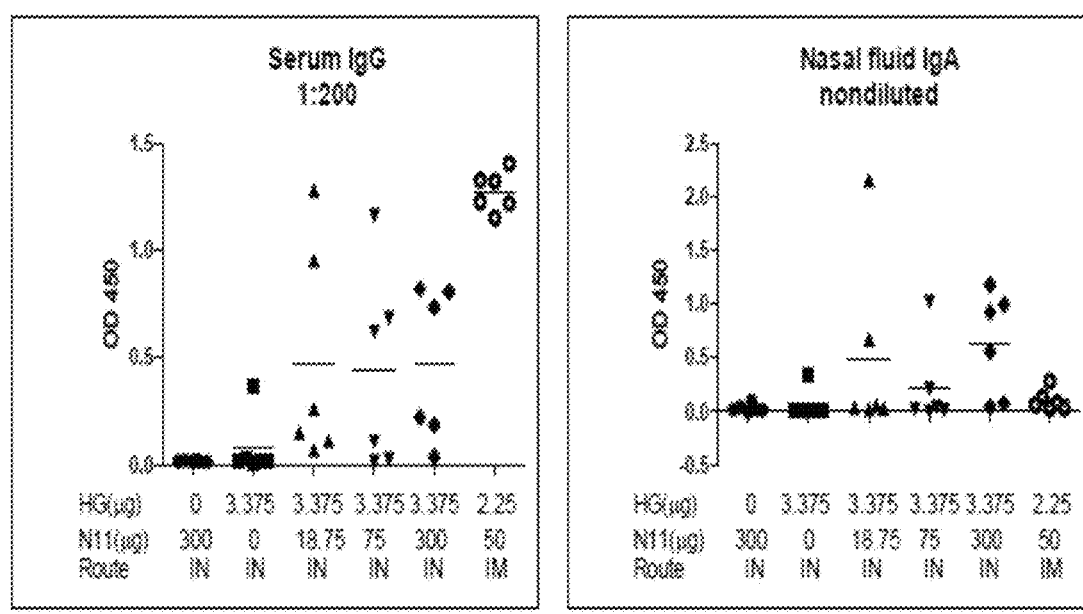
FIG. 14 is a graph showing Anti-H1 antibodies in serum (IgG) and nasal fluid after intranasal and intramuscular immunization. Each symbol represent a mouse.

The secretion of the active form of IL-1β is a two-step process. The first step involves the transcription of IL-1β DNA and synthesis of the inactive 31 kD pro-IL-1β. Pro-IL-1β is cleaved to 17 kD which is secreted. Cleavage of pro-IL-1β is usually mediated by caspase-1 which is a component of an inflammasome complex 22. Indeed, incubation with a caspase-1-specific inhibitor, YVAD, blocked the secretion of IL-1β induced by the adjuvant nanoparticles as shown in FIG. 6. Aluminum adjuvants activate the NLRP3 inflammasome and this involves a series of critical steps including phagocytosis of the particles, acidification of the phagosome, lysosome destabilization, and release of cathepsin B into cytosol. To study which pathways are involved in inflammasome activation by the adjuvant nanoparticles, different inhibitors were used and their effects on IL-1β production were checked. One hour before LPS priming, we applied these inhibitors to DCs while DMSO was used as a control. As expected, the secretion of IL-1β induced by aluminum adjuvants was inhibited by bafilomycin A1, cathepsin B inhibitor CA-074 Me, and YVAD as shown in FIG. 13. These results are consistent with the literature and similar findings have been reported for polystyrene and poly-lactide-glycolide nanoparticles. In contrast, only CA-074 Me inhibited IL-1β secretion following incubation with the adjuvant nanoparticles, whereas inhibition of endosome acidification had no effect as shown in FIG. 7. These results indicate that the adjuvant nanoparticles are capable of activating inflammasomes, but the mechanism of such activation is different from the commonly utilized route by aluminum adjuvants and other nanoparticles.

Figure 8:
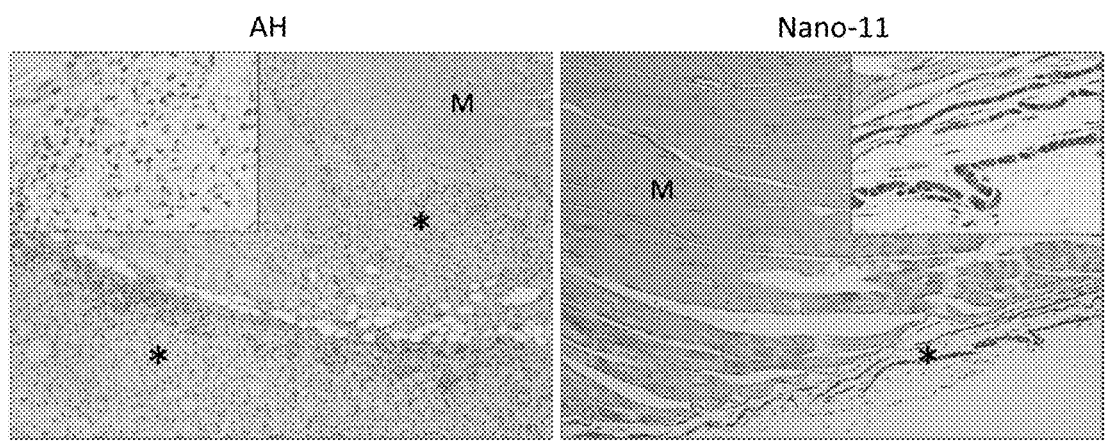
FIG. 8 shows the adjuvant nanoparticles cause less residual inflammation compared with aluminum hydroxide adjuvant (AH) where injection sites were collected 2 weeks after injection, and sections were stained with H&E. The images were collected with a 10× objective, inset 40×. *=inflammation; M=skeletal muscle.
Figure 12:
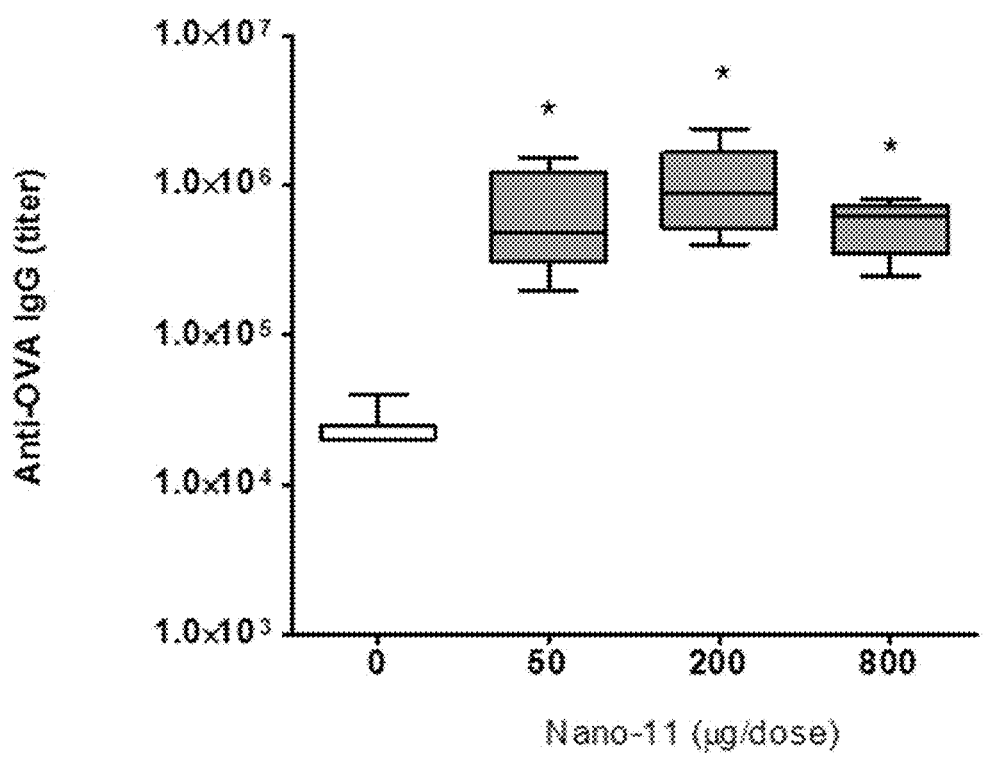
FIG. 12 is a graph demonstrating increased levels of OVA-specific IgG in mice injected with OVA with adjuvant nanoparticles. There was no difference between mice that received 50 μg, 200 μg, or 800 μg of adjuvant nanoparticles.

Referring now to FIG. 7, mice were injected intramuscularly with either soluble OVA or OVA formulated with different doses of that the adjuvant nanoparticles. The OVA-specific IgG titers after two injections were significantly increased for the mice that received the adjuvant nanoparticles. There was no significant difference in OVA-specific IgG between mice that received 50 µg, 200 µg, or 800 µg the adjuvant nanoparticles as shown in FIG. 12. The majority of IgG antibodies were IgG1 with little production of IgG2a antibodies. The experiment was repeated with a more relevant antigen, anthrax recombinant protective antigen (rPA), with similar results as shown in FIG. 8. These results show that the adjuvant nanoparticles strongly enhance the antibody response to two different antigens even at the low dose of 50 µg. During the experiments, none of the mice showed any signs of local irritation or systemic discomfort.

Local inflammation at the site of injection is thought to be important for activation of the adaptive immune response through the recruitment and activation of antigen-presenting cells 1. AF647-labeled adjuvant nanoparticles with OVA solution was injected into the one of the hind legs of BALB/c mice and soluble OVA only into the other leg. One day after injection, mice were euthanized. Their injection sites were excised, sectioned, and stained with monoclonal antibodies to detect inflammatory cells. The muscle injected with soluble OVA contained few inflammatory cells. In contrast, injection of the adjuvant nanoparticles—OVA induced the accumulation of many inflammatory cells including Mac-2-positive monocytes/macrophages, MHCII+ cells, and Ly-6G+ neutrophils. The macrophage marker F4/80 did not detect any cells in the injection site, suggesting that most of the Mac-2+ cells were monocytes or early stage macrophages. The Mac-2+ and MHCII+ cells contained intracellular adjuvant nanoparticles, indicating that they are the main cell types that took up the adjuvant nanoparticles in vivo. The relatively large number of monocytes and fewer neutrophils is different from the early inflammatory response following injection of aluminum adjuvant in which neutrophils are the most abundant cell type.

To examine the chronic inflammatory response, injection sites were examined two weeks following injection of either aluminum hydroxide adjuvant or the adjuvant nanoparticles with OVA. Light microscopy of H&E-stained sections revealed extensive granulomatous inflammation in muscle injected with aluminum adjuvants and much less inflammation following injection of the adjuvant nanoparticles as shown in FIG. 9. The granulomatous inflammation induced by aluminum adjuvant was comprised of extensive aggregates of macrophages containing aluminum adjuvant and scattered eosinophils. The adjuvant nanoparticles injection site contained relatively few macrophages arranged in slender cords in the connective tissue between muscle fibers. These results demonstrate the inflammatory response induced by the adjuvant nanoparticles is transient and resolves more quickly than the injection site reaction induced by aluminum hydroxide adjuvant.

Additional disclosure is found in Appendix-A filed herewith, the entirety of which is incorporated herein by reference into the present disclosure.

Those skilled in the art will recognize that numerous modifications can be made to the specific implementations described above. The implementations should not be limited to the particular limitations described. Other implementations may be possible.

References and citations to other documents, such as patents, patent applications, patent publications, journals, books, papers, web contents, have been made throughout this disclosure. All such documents are hereby incorporated herein by reference in their entirety for all purposes.

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected.

What is claimed is:

1. An overall positively charged vaccine adjuvant, comprising a core of alpha-D-glucan of at least 5% branch density and a plurality of binding moieties covalently bound to the core through hydroxyl groups on the core, wherein the plurality of binding moieties comprises hydrophobic groups and positively charged groups, wherein the molar ratio of positively charged groups versus hydrophobic groups is about 3:2, about 2:1, about 3:1, about 4:1, or about 5:1, the positively charged groups comprise ammonium ions or quaternary ammonium groups rendering the vaccine adjuvant positively charged in the pH range of 3 to 11, and the vaccine adjuvant ranges in size between 10 nanometers and 300 nanometers, and wherein the adjuvant is configured to adsorb negatively charged immunostimulatory molecules and to resist aggregation of the adjuvant nanoparticles.

2. The composition of claim 1; wherein the hydrophobic group includes a hydrocarbon chain.

3. The composition of claim 1; wherein the positively charged group is formed by reacting alpha-D-glucan with (3-chloro-2-hydroxypropyl)-trimethylammonium chloride, or CHPTAC.

4. The composition of claim 1; wherein the adjuvant ranges in size from 15 nm to 250 nm.

5. The composition of claim 1, wherein the adjuvant ranges in size from 20 to 200 nm.

6. A method of providing the vaccine adjuvant described in claim 1 comprising administering the adjuvant with at least one antigen to an animal to vaccinate against a disease.

7. The method of claim 6, wherein the vaccine adjuvant is provided in a dose range between 10 µg/dose to 10 mg/dose.

8. The method of claim 6, wherein the animal is a human.

9. The method of claim 6, wherein the disease is influenza.

10. A method of using the vaccine adjuvant of claim 1 as an immunotherapy, comprising administering the vaccine adjuvant with an antigen or antibody to an animal.

11. The composition of claim 1, wherein the alpha-D-glucan is selected from the group consisting of amylopectin, phytoglycogen, and glycogen.

12. The composition of claim 1, wherein the hydrophobic group is selected from the group consisting of alkyl group, alkene group, benzene group, sterol group, hydrophobic amino acids, cyclodextrins, aromatic hydrocarbons (arenes), alkanes, alkenes, cycloalkanes, and alkyne-based compounds.

13. The composition of claim 1 has the capacity to interact with negatively charged molecules selected from the group consisting of proteins, RNAs, DNAs, small molecules, and artificial oligonucleotides.

14. A composition comprising an overall positively charged vaccine adjuvant particulate comprising a structural core of highly branched phytoglycogen or glycogen, a plurality of hydrophobic groups covalently attached to the structural core through hydroxyl groups on the core, and a plurality of positively charged groups covalently attached to the structural core through hydroxyl groups on the core, wherein the molar ratio of positively charged groups versus hydrophobic groups is about 3:2, about 2:1, about 3:1, about 4:1, or about 5:1, wherein the adjuvant particulate ranges in size between 10 nanometers and 300 nanometers, and wherein the adjuvant is configured to adsorb negatively charged immunostimulatory molecules and to resist aggregation of the adjuvant nanoparticles.

15. The composition of claim 14, wherein the interactions of the adjuvant particulate with cells of the immune system result in phagocytosis by dendritic cells.

16. The composition of claim 14, wherein the interactions of the adjuvant particulate with cells of the immune system result in increased expression of costimulatory molecules.

17. The composition of claim 14, wherein the interactions of the adjuvant particulate with cells of the immune system result in increased secretion of IL-1β.

* * * * *